US009194828B2

(12) United States Patent
Turner

(10) Patent No.: US 9,194,828 B2
(45) Date of Patent: Nov. 24, 2015

(54) HANDHELD X-RAY SYSTEM FOR 3D SCATTER IMAGING

(71) Applicant: Aribex, Inc., Orem, UT (US)

(72) Inventor: D. Clark Turner, Payson, UT (US)

(73) Assignee: Aribex, Inc., Orem, UT (US)

( * ) Notice: Subject to any disclaimer, the term of this patent is extended or adjusted under 35 U.S.C. 154(b) by 20 days.

(21) Appl. No.: 13/900,299

(22) Filed: May 22, 2013

(65) Prior Publication Data

US 2013/0315369 A1    Nov. 28, 2013

Related U.S. Application Data

(60) Provisional application No. 61/650,354, filed on May 22, 2012.

(51) Int. Cl.
*G01N 23/203* (2006.01)
*H05G 1/06* (2006.01)
(Continued)

(52) U.S. Cl.
CPC ........ *G01N 23/203* (2013.01); *G01N 23/20008* (2013.01); *G01V 5/0025* (2013.01); *H05G 1/02* (2013.01); *H05G 1/06* (2013.01)

(58) Field of Classification Search
CPC ..... G01N 23/00; G01N 23/20; G01N 23/203; G01N 23/20008; G01V 5/0016; G01V 5/0025; H05G 1/00; H05G 1/02; H05G 1/04; H05G 1/06
USPC ......... 378/70, 86, 87, 89, 147, 149, 189, 193, 378/197, 198, 204, 210
See application file for complete search history.

(56) References Cited

U.S. PATENT DOCUMENTS 8,094,781 B1    1/2012 Safai et al.
2005/0117701 A1 *  6/2005 Nelson et al. .................. 378/87
(Continued)

FOREIGN PATENT DOCUMENTS

EP    2629083 A2    8/2013
JP    2009080032 A1    4/2009
(Continued)

OTHER PUBLICATIONS

European Patent Office, European Search Report for EP 13 16 8668, dated Sep. 20, 2013.

*Primary Examiner* — Anastasia Midkiff
(74) *Attorney, Agent, or Firm* — Kenneth E. Horton; Kirton McConkie

(57) ABSTRACT

Handheld imaging systems and methods for using such systems to create a 3D image of a desired object using scattered radiation are described. The handheld imaging apparatus can contain a housing, a radiation source for irradiating an object with a fan beam or cone beam, and multiple detector elements for detecting backscattered radiation from the object, where each detector element has a different view of the object and collects an image of the object that is different than the other detector elements. Alternatively, the handheld imaging apparatus can contain a housing, a radiation source for irradiating an object with a pencil beam of radiation, and a detector configured to detect backscattered radiation from the object, wherein the detector and the radiation source are oriented off-axis relative to each other. The handheld imaging apparatus are used to irradiate a desired object to obtain multiple two dimensional images of the object and then creates a three dimensional image of the object using the multiple two dimensional images. Other embodiments are described.

16 Claims, 12 Drawing Sheets

(51) Int. Cl.
*H05G 1/02* (2006.01)
*G01N 23/20* (2006.01)
*G01V 5/00* (2006.01)

(56) References Cited

U.S. PATENT DOCUMENTS

| | | |
|---|---|---|
| 2006/0256917 A1* | 11/2006 | Jacobs et al. .................... 378/76 |
| 2007/0001905 A1 | 1/2007 | Eronen |
| 2007/0002038 A1 | 1/2007 | Suzuki et al. |
| 2008/0019579 A1 | 1/2008 | Crucs |
| 2008/0253511 A1 | 10/2008 | Boyden et al. |
| 2008/0285715 A1* | 11/2008 | Shedlock et al. ............... 378/87 |
| 2009/0060145 A1 | 3/2009 | Tranchant et al. |
| 2012/0045127 A1* | 2/2012 | Song et al. .................... 382/171 |

FOREIGN PATENT DOCUMENTS

| | | |
|---|---|---|
| WO | 2005081956 A2 | 9/2005 |
| WO | 2006023674 A1 | 3/2006 |
| WO | 2007149402 A2 | 12/2007 |
| WO | 2009134849 A2 | 11/2009 |
| WO | 2011141763 A1 | 11/2011 |
| WO | 2012166262 A2 | 12/2012 |

* cited by examiner

HANDHELD X-RAY SYSTEM FOR 3D SCATTER IMAGING

CROSS-REFERENCE TO RELATED APPLICATIONS

This application claims priority to U.S. Provisional Patent Application 61/650,354, filed May 22, 2012 and entitled "Handheld X-Ray System for 3D Backscatter Imaging", the entire disclosure which is incorporated herein by reference.

FIELD

This application relates generally to handheld imaging systems and methods for using such systems to create an image of a desired object using scattered radiation. More particularly, this application relates to handheld x-ray systems and methods for using such systems to create a three dimensional (3D) image of a desired object using scattered radiation.

BACKGROUND

In many industrial, military, security or medical applications, images of an internal structure of objects are required. Radiography is one type of technique that can be used for imaging. Radiography generally comprises either conventional transmission radiography or backscatter radiography. When access behind an object to be interrogated is not possible, only backscatter radiography is possible. One method of backscatter imaging is Compton Backscatter Imaging (CBI), which is based on Compton scattering.

Lateral migration radiography (LMR) is one type of imaging based on CBI that utilizes both multiple-scatter and single-scatter photons. LMR uses two pairs of detector with each pair having a detector that is uncollimated to predominantly image single-scatter photons and the other detector collimated to image predominantly multiple-scattered photons. This allows generation of two separate images, one containing primarily surface features and the other containing primarily subsurface features.

Recently, backscatter radiography by selective detection (RSD), a variant of LMR, has been used. RSD uses a combination of single-scatter and multiple-scatter photons from a projected area below a collimation plane to generate an image. As a result, the image has a combination of first-scatter and multiple-scatter components, offering an improved subsurface resolution of the image.

SUMMARY

This application relates to handheld imaging systems and methods for using such systems to create a 3D image of a desired object using scattered radiation. The handheld imaging apparatus can contain a radiation source for irradiating an object with a fan beam or cone beam, and multiple detector elements for detecting backscattered radiation from the object, where each detector element has a different view of the object and collects an image of the object that is different than the other detector elements. Alternatively, the handheld imaging apparatus can contain a radiation source for irradiating an object with a pencil beam of radiation, and a detector configured to detect backscattered radiation from the object, wherein the detector and the radiation source are oriented off-axis relative to each other. The handheld imaging apparatus are used to irradiate a desired object to obtain multiple two dimensional images of the object and then creates a three dimensional image of the object using the multiple two dimensional images.

BRIEF DESCRIPTION OF THE DRAWINGS

The following description can be better understood in light of the Figures, in which:

FIG. 2b comprises a three-dimensional image obtained by using a reconstruction method on the images obtained in FIG. 2a;

Figure 1:
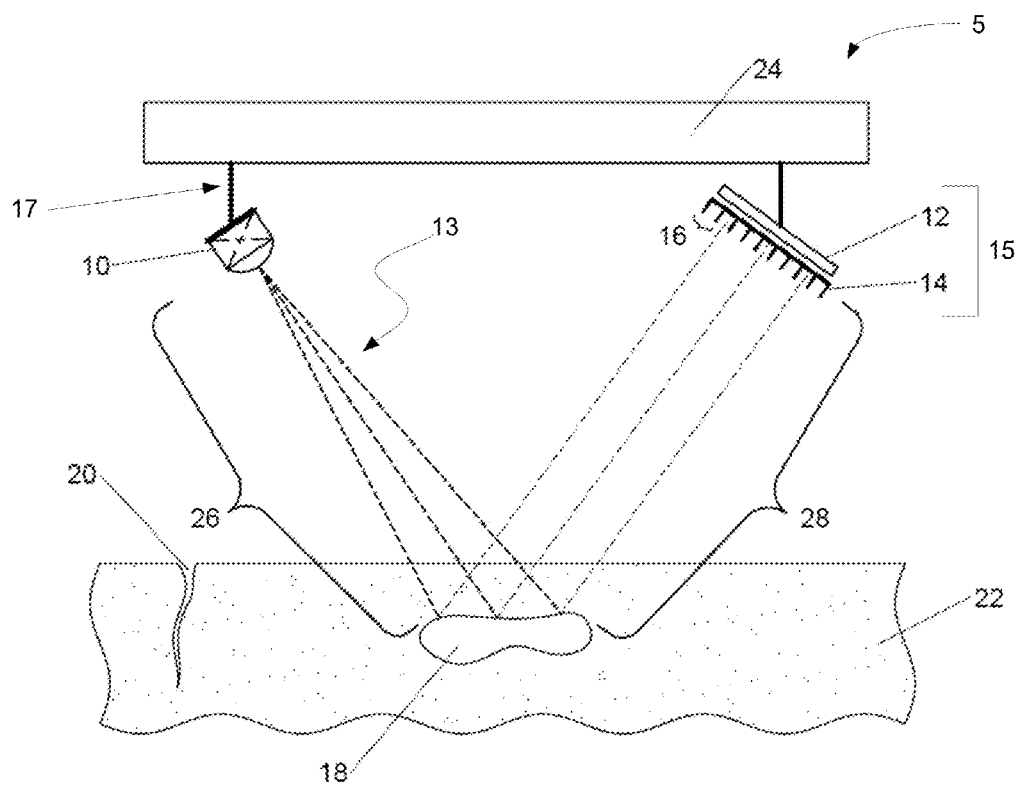
FIG. 1 illustrates some embodiments of an imaging system using radiography to detect backscattering.

The Figures illustrate specific aspects of the handheld systems and methods for using the handheld x-ray systems to create 3D images based on backscattered x-rays. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, the Figures may show simplified or partial views, and the dimensions of elements in the Figures may be exaggerated or otherwise not in proportion for clarity.

DETAILED DESCRIPTION

The following description supplies specific details in order to provide a thorough understanding. Nevertheless, the skilled artisan will understand that the described imaging system and associated methods of making and using the system can be implemented and used without employing these specific details. Indeed, the imaging system and associated methods can be placed into practice by modifying the described systems and methods and can be used in conjunction with any other apparatus and techniques conventionally used in the industry. For example, while the description below focuses on using the imaging system for backscatter x-rays, it could be used for other types of radiations, such as gamma rays, neutrons, electron beams, or combinations thereof.

As the terms on, attached to, or coupled to are used herein, one object (e.g., a material, a layer, a substrate, etc.) can be on, attached to, or coupled to another object regardless of whether the one object is directly on, attached, or coupled to the other object or there are one or more intervening objects between the one object and the other object. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

Some embodiments of non-handheld imaging systems and methods for using such systems to create an image of a desired object using scattered radiation (including backscattered radiation) are shown in FIGS. 1-4. FIG. 1 illustrates a schematic representation of a non-handheld imaging system which can be used for detecting backscattered radiation. As used herein, scattering radiation includes any backscattering (with an angle less than about 90 degrees) or forward scattering radiation (with an angle of 91 to 180 degrees) occurring away from the surface of the irradiated object or material.

The system 5 contains a source of radiation 10. The radiation source (or source) 10 can be any source (or sources) of radiation that penetrates the desired object (or objects), including an x-ray source, a gamma ray source, a neutron source, an electron beam source, or combinations thereof. The source 10 irradiates the desired object area (including the object itself) using the desired type of radiation to a desired depth.

In some embodiments, the amount of radiation (or intensity) from the source 10 can be controlled and customized for a specific object. For example, the radiation source 10 can be controlled to provide a photon illumination (energy) spectrum with an average depth in the object to obtain the detail needed to create an image. In another example, the radiation intensity provided by radiation source 10 can be sufficiently low so as to not saturate the detector 12 (described below).

As shown in FIG. 1, the radiation source 10 transmits radiation 26 which partially or completely penetrates the surface of a material 22 that is part of an object or object volume to be analyzed. The radiation 26 strikes internal portions of the material 22, such as cracks 20, voids 18, or hidden objects in the material 22. Those internal portions in the material 22 then backscatter a portion of the radiation 26 as backscattered radiation 28. In some configurations, the radiation source 10 is also capable of independent motion in different directions including rotation, in-and-out movement of the radiation source 10 from the object region, and angular movement. The radiation source 10 can be adjusted to select or focus on the object that is being analyzed or scanner by the beam 13 of radiation 26. Alternatively, the radiation source can be stationary and the object can be movable.

The beam 13 from the radiation source 10 can be configured to be any type of known beam. In some configurations, the beam can be configured as a pencil beam, fan beam, cone beam, or combinations thereof. In some instances, a fan beam or cone beam can be used since they can create a higher intensity backscatter field and have a larger field of view than a pencil beam, thereby saving time due to the simultaneous collection from a larger field of view. The width and/or length of the fan and/or cone beam can be adjusted to enhance the resolution of the image.

Where a fan beam is used, it can be configured by utilizing an aperture. In these embodiments, the beam of radiation can be passed through the aperture such that the output from the aperture is a fan beam of radiation. These embodiments can increase the analysis speed by radiating a line of the object, instead of only a spot radiated by a pencil beam, and by using the fan beam to create a higher intensity backscatter field.

The system 5 also contains a detector 12. The detector 12 can be any detector (or detectors) of radiation that can detect the radiation scattered from the object. In some embodiments, the detector can include an x-ray detector, a gamma ray detector, a neutron detector, an electron beam detector, or combinations thereof. In other embodiments, the detector 12 can comprise NaI scintillator crystals, plastic scintillators, photostimuable phosphor-based image plates, TFT-based flat panel detectors, amorphous silicon panels, or combinations thereof. For example, for x-ray radiography on a large area image, a photostimuable phosphor-based imaging plate and/or an amorphous silicon panel (ASP) conversion screen bonded to an array of photosensitive diodes.

The detector(s) can be separated into multiple detector segments that each detects radiation along a single path or line of sight. This separation can be accomplished using any mechanism that isolates each segment so that it only receives radiation along that path. For example, in the embodiments depicted in FIG. 1, the detector 12 comprises a collimator 14 coupled to the detector 12 and so is referred to as a collimated detector 15. The collimator contains multiple detector segments within each grid of the collimator. In the embodiments depicted in FIG. 1, the radiation source 10 and the collimated detector 15 can be disposed on the same side of the object region to be analyzed. The radiation source 10 can generate photons that are directed toward the object region. The collimated detector 15 collects photons that are backscattered from the surfaces of the object and from objects hidden or voids beneath the surfaces. The collimated detector not only detects the backscattered radiation, but also assists in generating three-dimensional images of the object area, including hidden objects and/or voids.

The collimator 14 can include any of a variety of cross sectional areas, including a cylindrical, elliptical (non-circular), or rectangular. In some embodiments, the collimator 14 and the detector 12 have the shape so that any or all of the backscattered radiation that travels through the collimator 14 is detected. The collimator 14 may include any number of collimator features with various geometries including fins, slats, screens, and/or plates that may be curvilinear or flat. In some embodiments, the collimator 14 (and such features) can be formed from any known radiation absorbing material, such as lead. In other embodiments, the collimator 14 (and such features) can be formed from radiation reflective material, such as high density plastic, aluminum, or combinations thereof. These latter embodiments are helpful when enhancement, rather than removal, of certain backscatter radiation is desired. In some configurations, the collimator features can be oriented substantially perpendicular to the surface of the detector 12. In other configurations, the collimator features can be given any orientation relative to the detector 12 that provides the desired line of sight radiation for each segment.

In some configurations, the separation of the detector using the collimator can create apertures 16. Backscattered radiation from the object reaches the detector 12 through the apertures 16 if the backscatter direction is substantially parallel to the collimator features or has a narrow enough angle to travel through the aperture without being absorbed by the collimator feature. The collimator features can be modified to allow for a wider aperture to allow in more backscattered radiation or a narrower aperture to decrease the backscattered radiation from the object.

In some embodiments, the collimator 14 may be adjustable to alter the direction of the backscattered radiation which can reach the detector. In these embodiments, the position and/or orientation of the collimator features can be modified to change the position and/or orientation by manual mechanisms or by automatic mechanisms, such as through computer controlled motor drives.

The collimator 14 can be coupled to the detector using any known technique. In some embodiments, the collimator 14 can be optically coupled to the detector 12 so that radiation passing by the collimator 14 reaches the detector 12 and is measured, creating a collimated detector 15. In other embodiments, the collimator 14 can be physically attached to the detector 12.

The collimated detector 15 can move in different directions including rotation, in-and-out movement from the object region, and angular movement. In some configurations, the collimator 14 can move in different directions relative to the detector, including rotation, in-and-out movement, and angular movement. These movements can focus the image by selecting and/or isolating the desired backscattered radiation. In other words, adjusting the collimated detector 15 allows the user to select and isolate particular vectors of backscattered radiation to travel through the aperture 16 and be detected by the detector 12. Alternatively, the collimated detector can be stationary and the object movable.

In some embodiments, the radiation source 10 and the collimated detector 15 may be attached to a moving structure (such as plate 24), as shown in FIG. 1. The plate 24 has a movement axis that is substantially perpendicular to the object. In some embodiments, this movement axis is a rotational axis and so the plate 24 is a rotational plate. (Such rotational axis is shown as axis 35 in FIG. 2a.) The radiation source 10 and collimated detector 15 may be attached to the plate 24 as known in the art, such as poles 17 extending from the rotating plate 24. The radiation source 10 and collimated detector 15 may be located at any location along the plate 24 and this location can be fixed or altered as desired. This configuration allows both the collimated detector 15 to detect backscatter and the source 10 to irradiate the object from any location along the plate 24.

In these embodiments, the rotational axis of the plate 24 allows the source 10 and collimated detector 15 to be rotated about the object region while maintaining a similar distance and orientation from the object. Independent adjustments can be made to the source 10 and collimated detector 15 to change the distance and orientation from the object, if needed. In some configurations, the plate 24 may comprise a single plate so the source 10 and the collimated detector 15 remain at about an 180° angle relative each other. In other configurations, the plate 24 may be two plates, attached or separate, to allow the radiation source 10 and collimated detector 15 to be rotated independently and oriented at any desired angle relative to each other. For example, the radiation source 10 may remain in a fixed position while the collimated detector 15 can be rotated to create various angles of orientation relative to the source 10.

In some embodiments, the system 5 can be contained in a protective and supportive housing which can be made from any known flexible and/or known lightweight materials. The housing holds the various components of the system 5 in place. Lightweight housing materials facilitate portability of the system, which can be advantageous in certain applications. Using such materials also allows the housing to be manufactured in a variety of desired shapes and allows the system to be relatively lightweight to make it easy to transport. In some embodiments, the system 5 can be configured as a compact system so that it is readily transportable and adopted to work within confined spaces.

Figure 2B:
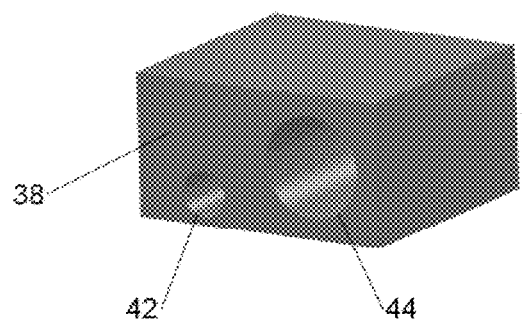
Figure 2A:
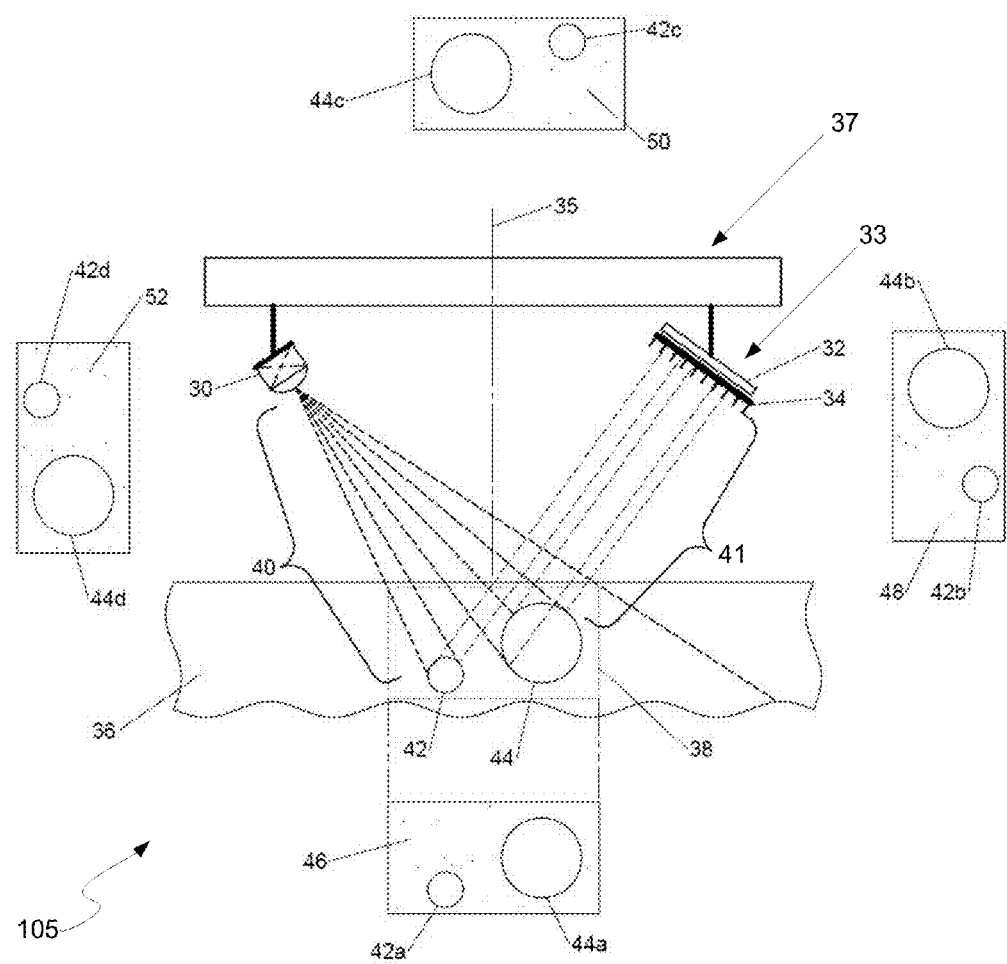
FIG. 2a depicts other embodiments of the imaging system and the images obtained from the system.

In some embodiments, the system 105 can be used to detect backscattered radiation, as shown in FIG. 2a. In this Figure, a radiation source 30 transmits radiation 40 which penetrates the surface of a material 36 and strikes internal details such as voids 42 and 44, hidden objects, and/or cracks (not shown) in the material 36. These internal details in the material 36 then backscatter a portion of the transmitted radiation 41. The backscatter 41 can pass through a collimator 34 and be detected by the detector 32.

In these embodiments, the radiation source 30 can generate photons that are directed toward an object (including object region 38) and the collimated detector 33 collects photons that are backscattered from the scanned surface and from the internal details beneath the scanned surface. The object region 38 can be shifted by independent adjustments to the radiation source 30 or by changing the location of the radiation source 30 along a rotating plate 37. For example, adjustments can be made to the object region 38 by changing the distance from the radiation source 30 to the object region 38, which will shrink or enlarge amount of the object region 38 being irradiated. Further, the object region 38 can be shifted by changing the angle of the radiation source 30 with respect to the object region 38.

In these embodiments, the beam from the radiation source 30 may be a pencil beam, a fan beam, or a cone beam. With a cone beam it is possible to scan the entire object region 38 without the need to move or modify the radiation source 30. The cone beam may also be moved to increase or decrease the size of the object region. When using a pencil beam or fan beam, it can scan a specific part of the object region 38. The imaging system 105 can use any scanning design, including raster scanning, to create a desired object region 38. The object region 38 can be a variety of cross sectional areas, including cylindrical, elliptical (non-circular), or rectangular (includes square). As explained in further detail below, data gathered from multiple orientations of the radiation source 30 and collimated detector 33 should be of approximately the same object region 38.

The configuration of the radiation source 30 and the collimated detector 33 allow the acquisition of multiple sets of data or images from the object region 38. Therefore, it is possible to obtain multiple images of the same object region 38 from different orientations between the radiation source 30 and the collimated detector 33. In some embodiments, the orientation between the source 30 and the collimated detector 33 can range from about 1° up to about 359° relative to each other. For example, an image of an object region 38 may be collected when the radiation source 30 and the collimated detector 33 are initially at a 180° angle with respect to each other, and thereafter the radiation source 30 can be rotated in 10° increments around the object region 38, collecting an image at each location. The subsequent application of a computer model on these multiple images will allow a three-dimensional reconstruction of the object region 38.

As shown in FIG. 2a, multiple images 46, 48, 50, and 52 can be taken from various configurations of the radiation source 30 and the collimated detector 33. Although FIG. 2a depicts four images, any number of images could be used to obtain a three-dimensional reconstruction. In some embodiments, the number of images can range from 2 (with appropriate constraints) to any desired number. In other embodiments, the number of images can range from 3 or 4 to 10 or 15. Of course, the more images that are taken, the better the resolution of the 3D reconstruction.

Image 46 can be obtained by data collected from the configuration of the source 30 and collimated detector 33 depicted in FIG. 2a. The voids 42 and 44 found in the material 36 can be depicted in image 46 as two-dimensional objects 42a and 44a. Image 48 can be obtained by rotating the radiation source 30 and/or the collimated detector 33 by the desired amount and collecting additional data to depict the voids 42 and 44 as two-dimensional objects 42b and 44b. To obtain image 48, the radiation source 30 and collimated detector 33 were both rotated 90° about the object region 38 in the same direction (e.g. remaining at a 180° angle with respect to each other). Image 50 can be obtained by rotating both the radiation source 30 and collimated detector 33 another 90° about the object region 38 in the same direction depicting the voids 42 and 44 as two-dimensional objects 42c and 44c. In some configurations, the configuration used to generate image 50 could be the minor image of the configuration shown in FIG. 2a, having the radiation source 30 located on the right side of the system and the collimated detector located on the left side of the system. Image 52 is obtained by again rotating the radiation source 30 and collimated detector 33 another 90° about the object region 38 in the same direction depicting the voids 42 and 44 as two-dimensional objects 42d and 44d.

Rotation about the object region 38 can be accomplished by rotating plate 37 around rotational axis 35 that is oriented substantially perpendicular to the material 36. In these embodiments, the plate 37 may be a single plate that rotates the radiation source 30 and collimated detector 33 at the same rotational distance from each other (i.e. the radiation source 30 and collimated detector 33 remain 180° from each other). In other embodiments, the plate 37 may be two plates, attached or separate, that allow the radiation source 30 and collimated detector 33 to rotate at different rotational distances with respect to each other. Rotation about the object region can also be accomplished by keeping the radiation source 30 and collimated detector 33 stationary and rotating the object region 38.

FIG. 2b depicts a three-dimensional (3D) structure of the object region 38 and voids 42 and 44 using the images 46, 48, 50, and 52. This 3D structure can be obtained using the reconstruction method described herein. The reconstruction method can be used to supply a three-dimensional structure of any desired feature of the material 36, including voids, cracks, corrosion, delaminations, or other hidden objects.

The mathematical formulation, which gives rise to a forward or generative model, for use in reconstruction is as follows. The formulation only considers photons returning to the detector from a single backscatter rather than multiple scattering events. The collimated detector establishes a set of apertures each of which has an associated line of sight. Incident photons move along the associated line of sight, which is a three-dimensional space defined by the location and orientation of the aperture.

Figure 3:
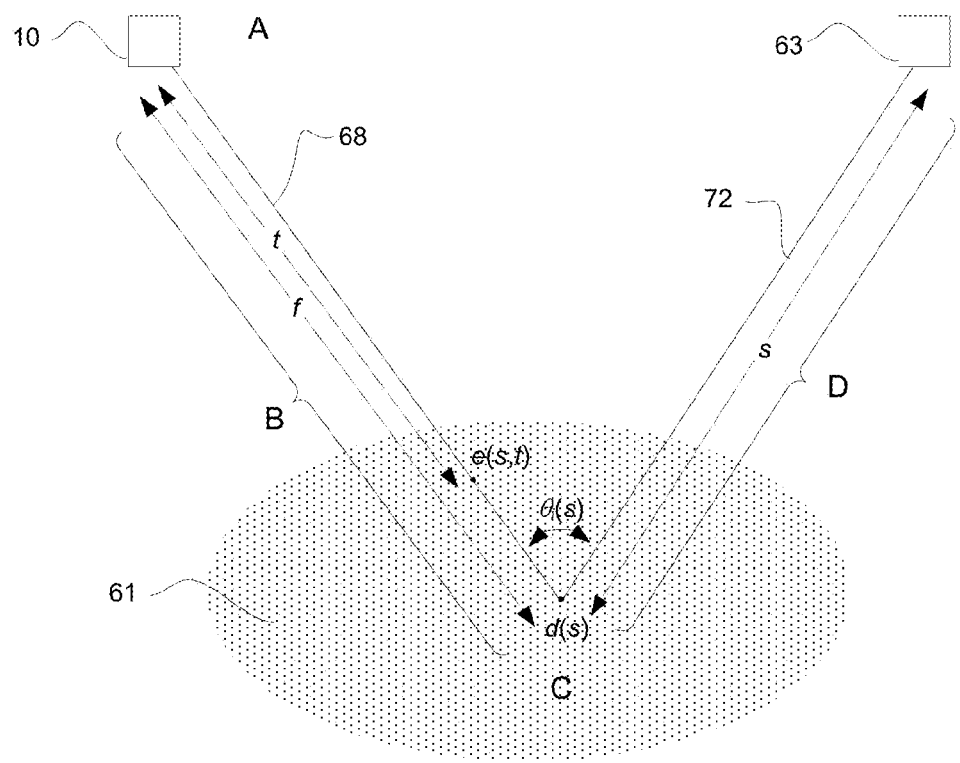
FIG. 3 illustrates some embodiments of simulation details that can be used in the reconstruction method.

FIG. 3 shows the simulation details for an embodiment of the reconstruction method. The region of space 61 to be imaged is called the object region. The position along collimated line 72 a distance s from the detector segment 63 is referred to as d(s). For the purposes of this discussion detector segment 63 may be a portion of detectors, such as detector 12 or 32 discussed above. Line 68 connects d(s) with source 10. The position along the line 68 a distance t from the radiation source is referred to as e(s,t). The distance from d(s) to the radiation source 10 is referred to as f.

The expression for the number of photons, or signal intensity, reaching the detector segment 63 from backscatter at d(s) can include four terms: (A) the number of photons radiated from the radiation source 10, (B) the loss of intensity traveling along line 68 from the radiation source 10 as it passes through a material in the object region to reach d(s), (C) the fraction of that intensity that is scattered along line 72, and (D) the loss of intensity as the backscattered photons travel along line 72 to the detector. The cumulative effects of terms A, B, C, and D are multiplicative and thus the mathematical expression for the intensity reaching the detector along a single path i, from a backscatter at a distance s is:

$$E_i(s) = A \times B \times C \times D = E_0 e^{-\int_0^f \rho(e_i(t,s))dt} \gamma(\theta_i(s)) \rho(d_i(s)) e^{-\int_s^0 \rho(d_i(q))dq}, \quad (1)$$

where $E_0$ is the intensity of the radiation source 10, $\rho(x)$ is the material density as a function of the position x in the object region, $\theta_i(s)$ is the angle formed by the two lines 68 and 72, and $\gamma(\theta_i(s))$ is the differential scattering cross section as a function of the angle at which the two lines meet. In order to model the effects of Compton scattering $\gamma(\theta_i(s))$ can be set equal to $\cos^2(\theta)$. Alternatively, other models of the scattering can be used and substituted into equation (1).

The total intensity traveling along path i is the integral of all the backscatter events along the line 72. This is:

$$E_i = \int_0^\infty E_i(s)ds = E_0 \int_0^\infty e^{\int_0^f \rho(e_i(t,s))dt} \gamma(\theta_i(s)) \rho(d_i(s)) e^{\int_s^0 \rho(d_i(q))dq} ds, \quad (2)$$

where, in practice, the integral along d(s) ends at the effective boundaries of the object region (i.e. no material or signal becomes insignificant).

The basic form of equations 1 and 2, unlike conventional tomography or tomosynthesis, does not lend itself to an easy decomposition into linear expressions of $\rho$, the image density. Rather there is a nonlinear mixture of terms—a combination of the multiplicative effect of the backscattering term with the exponential terms that model the intensity loss and the composition of backscattering along the line of sight, represented as the outermost integral in Equation 2.

For reconstruction the term $A=E_0$ can be treated as a constant and absorbed into the detector units. The constant can be estimated globally or measured separately before imaging. The form for Equation 2 in terms of the integral along the detector segment line of sight and the image density therefore becomes:

$$\frac{E_i}{E_0} = \int_0^\infty B_i(\rho, s) C_i(s) \rho(d_i(s)) D_i(\rho, s) ds, \quad (3)$$

where the functions $B_i$ and $D_i$ are nonlinear functions of $\rho$.

By treating the nonlinear interactions as secondary and using a fixed estimate for $\rho$, denoted as $\hat{\rho}$, the equation becomes:

$$M_i = \frac{E_i}{E_0} = \int_0^\infty B_i(\rho, s) C_i(s) \rho(d_i(s)) D_i(\rho, s) \, ds = \int_0^\infty w_i(s) \rho(d_i(s)), \quad (4)$$

where the terms that do not depend explicitly on ρ into $w_i(s)$ are combined. The result is a linear operator, and thus, an expression for the image formulation that is of the same form as a conventional x-ray formation—and, by analogy, tomographic reconstruction.

Considering the discrete form of Equation 4, the approximation of ρ on a grid or individual detector segment is denoted as $R_k$, the value of ρ at a grid location is denoted as $X_k$, and the number of projection images collected as N. The discrete reconstruction $R_k$ is designed to optimize the total difference between the measured detector intensities and those simulated from applying the imaging model to the discrete reconstruction, $R_k$. As shown in equation (4), the function $w_i(s)$ can be captured as a set of weights $W_{ij}$ that measures the relationship between the fixed estimated $\hat{\rho}$, the solution on the grid $R_k$ where the backscatter occurs, and the corresponding line integrals from the radiation source 10 and detector segment 63 to the point. Then the reconstruction is formulated as:

$$R = \mathrm{argmax}_R \sum_{j=1}^{N} \left( \sum_{i=1}^{M} W_{ij} R_j - M_i \right)^2, \quad (5)$$

where M is the number of grid points (e.g., detector segments) in the reconstruction, and R represents the entire collection of grid points in the solution. R represents the object that is to be reconstructed and M represents the projection data collected. The weights $W_{ij}$ can be computed in a manner that is similar to conventional computer tomography, that is, by using a linear interpolation (e.g. trilinear in 3D) and using the geometric relationships between the grid and the line integral to establish this linear dependence for each pair of points on the detector and the reconstruction grid.

The least squares problem in Equation (5) can be solved as an over-constrained linear system. The linear system in Equation (5) can be solved in a variety of ways including standard numerical relaxation (linear system) methods and conventional iterative methods such as the algebraic reconstruction technique (ART) or simultaneous algebraic reconstruction technique (SART). If SART is used, the algorithm formulates the reconstruction problem as finding an array of unknown variables using algebraic equations from the projection data. It is an iterative reconstruction algorithm, which has the advantage of robustness to noise and incomplete projection data. As the ART and SART algorithms, and variations thereof, are known to one of skill in the art, they will not be described further.

Due to the nature of the formulation and underlying physics, $\hat{\rho}$ can be treated as fixed. Because the integrals in Equation (4) average (or smooth) the effects of the material properties between source-detector and position of the backscatter, and thus, aggregate material properties along the rays is sufficient to obtain some level of accuracy in the reconstruction.

The accuracy results depend on the accuracy of the models of the intensity loss that takes places as radiation moves to and from the point of backscatter. Iterative reconstruction can be used, denoting as a sequence of solutions $R^0, R^1, R^2, \ldots$, and a sequence of discrete estimates of the solution used to model intensity loss $\hat{R}^0, \hat{R}^1, \hat{R}^2, \ldots$. This gives a sequence of weights in the linear system, $W^l_{ij}$. In implementation, the estimates of $\hat{R}^j$ simply lag in the formulation. In this way $\hat{R}^l = R^{l-1}$ and $W^l$ can be computed from the intensity loss estimated from the previous solution and they change with each subsequent iteration. Such schemes can be effective for nonlinear optimization problem (i.e., let the nonlinear terms lag).

Some embodiments pertain to a method and apparatus for a single-sided, non-destructive imaging technique utilizing the penetrating power of radiation to image subsurface and surface features. These embodiments can be used for a variety of applications including non-destructive examination, medical imaging, military, and security purposes.

Figure 4:
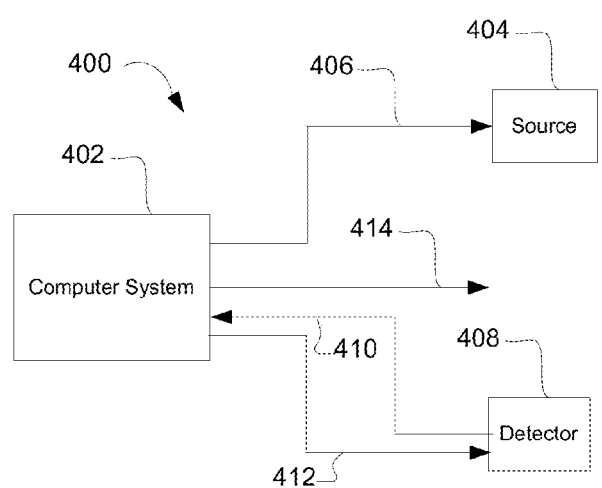
FIG. 4 illustrates a block diagram backscatter imaging system in accordance with some embodiments of the invention.

Implementation of the reconstruction algorithms can be conveniently performed using various means for reconstruction. In some embodiments, a conventional processing system (such as, for example, a computer) can provide a means for reconstruction using computer tomography. In particular, the algorithms can be implemented in software for execution on one or more general purpose or specialized processor(s). The software can be compiled or interpreted to produce machine executable instructions that are executed by the processor(s). The processor can accept as inputs any of the following:

a. Orientation/position of the object relative to the source
   b. Orientation/position of the object relative to the detector
   c. Output signal (array of signals) from the detector If desired, the processor can also control the relative positioning of the object relative to the source and detector. Thus, the processor can output any of the following:

a. Rotational control for the object
   b. Linear positioning control for the source
   c. Linear positioning control for the detector FIG. 4 illustrates an example of a system for backscatter imaging. The system 400 can include a computer subsystem 402 (which can, for example, be a personal computer, tablet computer, workstation, web server, or the like). In some embodiments, the computer subsystem 402 may comprise multiple devices that share computing resources. For example, the computer subsystem 402 may include computational capacity in the handheld device and the capacities in a tablet computer, which may be used to display the rendered images to a user. The computer system can be of conventional design, including a processor, memory (data storage and program storage), and input/output. The computer system can include a display (e.g., for displaying reconstructed images) and human input devices (e.g., keyboard, mouse, tablet, etc.). The computer system can interface to a radiation source 404, to and provide control information 406 to the radiation source. For example, control information can provide for turning on/off the radiation output of the source and setting the source output intensity. The system can include mechanical means (e.g., as described above) for moving the source, in which case the control information can also control the position/orientation of the source.

The system 400 can also include a detector 408 which can provide measurements 410 of detected backscattered radiation to the computer system 402. For example, the measurements can be digital data provided from the detector. As another example, the measurements can be analog data, and can be converted (e.g., using an analog to digital converter) into digital form before processing. The system can include mechanical means (e.g., as described above) for moving the detector, in which case control information 412 can be provided from the computer system to the detector to control the position/orientation of the detector.

The computer system 402 can be programmed to implement reconstruction techniques (e.g., as described above) to combine data from multiple two-dimensional slices of detected backscattered radiation 410 to form a three-dimensional reconstructed image. The three-dimensional reconstructed image can be output for display, stored in a memory for later use, or transmitted via a communications link (e.g., the Internet) to another location for display or storage. In some embodiments, the system 400 can also include mechanisms for moving the object to be imaged (e.g., as described above) in which case the computer system 402 can provide control output 414 for controlling the position/orientation of the object.

These imaging systems described above can be used to detecting flaws and defects in materials and structures, scanners for detecting target objects and/or foreign object debris inside of walls and structures, devices for security purposes to identify objects hidden in walls, containers or on individuals, portal scanning, law enforcement and other security applications, and medical imaging.

Some conventional x-ray systems use a collimated moving pencil beam of x-rays to irradiate the sample and a large area-detector to collect the scattered x-rays. For 3-D imaging, the collimated detectors are used to collect x-rays from a known scattering angle, and the sample is raster scanned to get the x-y information. The depth information can be collected at the intersection of the collimated x-ray beam and collimated detector. Some of these systems provide only a 2-D image, without any depth information to show the location of the feature of interest below the surface. On the other hand, a 3-D imaging method can be used determine the location of a feature of interest within a larger volume.

The x-ray systems and methods described above improve on some conventional x-ray systems by using a collimated multi-element detector array and a fan or cone-beam x-ray source to collect a complete 2-D scatter image. The assembly is then rotated in space to obtain multiple 2-D images from which a 3-D computed tomography reconstructed image can be obtained. But still the systems described above can be bulky and heavy since large components are used in order to obtain a high image resolution. In fact, such systems are not handheld because the weight of the systems can often be about 200 lbs.

Figure 14:
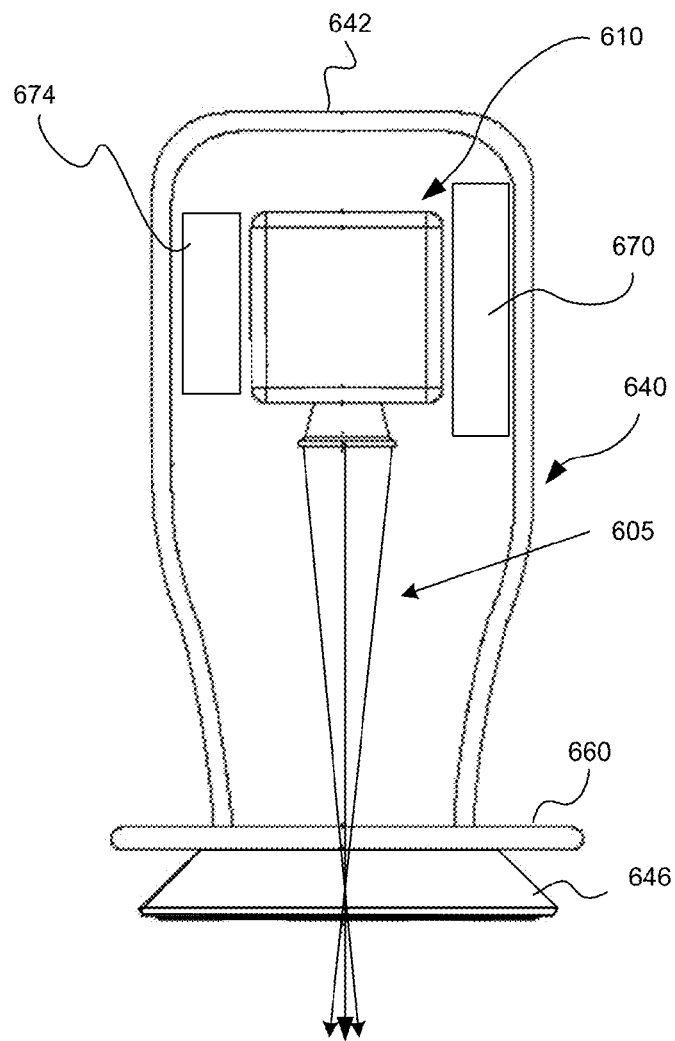
FIGS. 14 and 15 depict side views of other embodiments of a handheld imaging apparatus.
Figure 14:
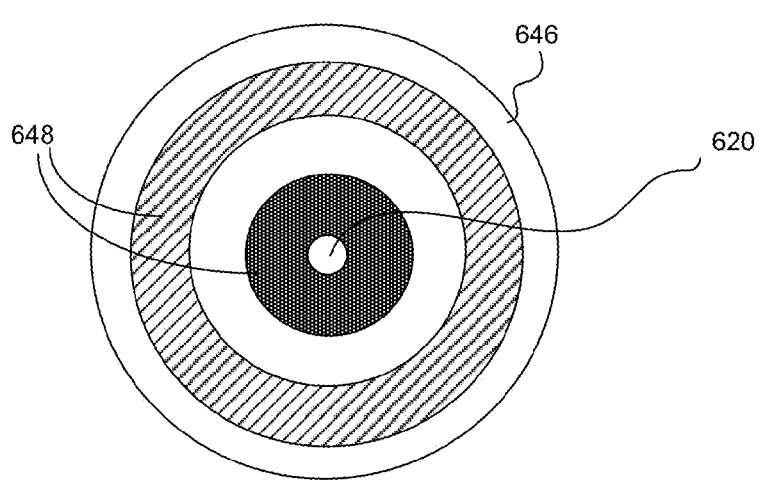
Figure 15:
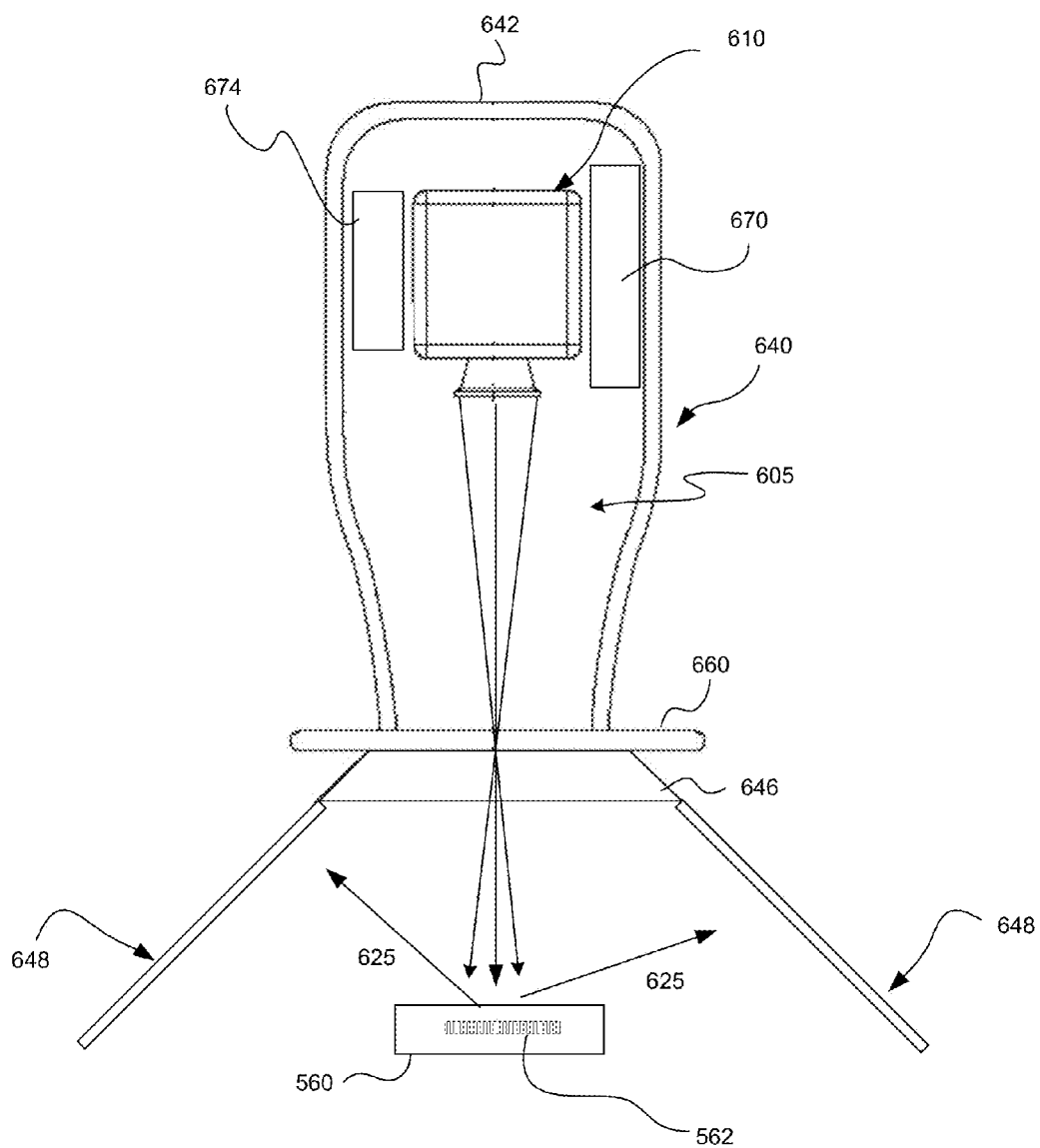
Figure 16:
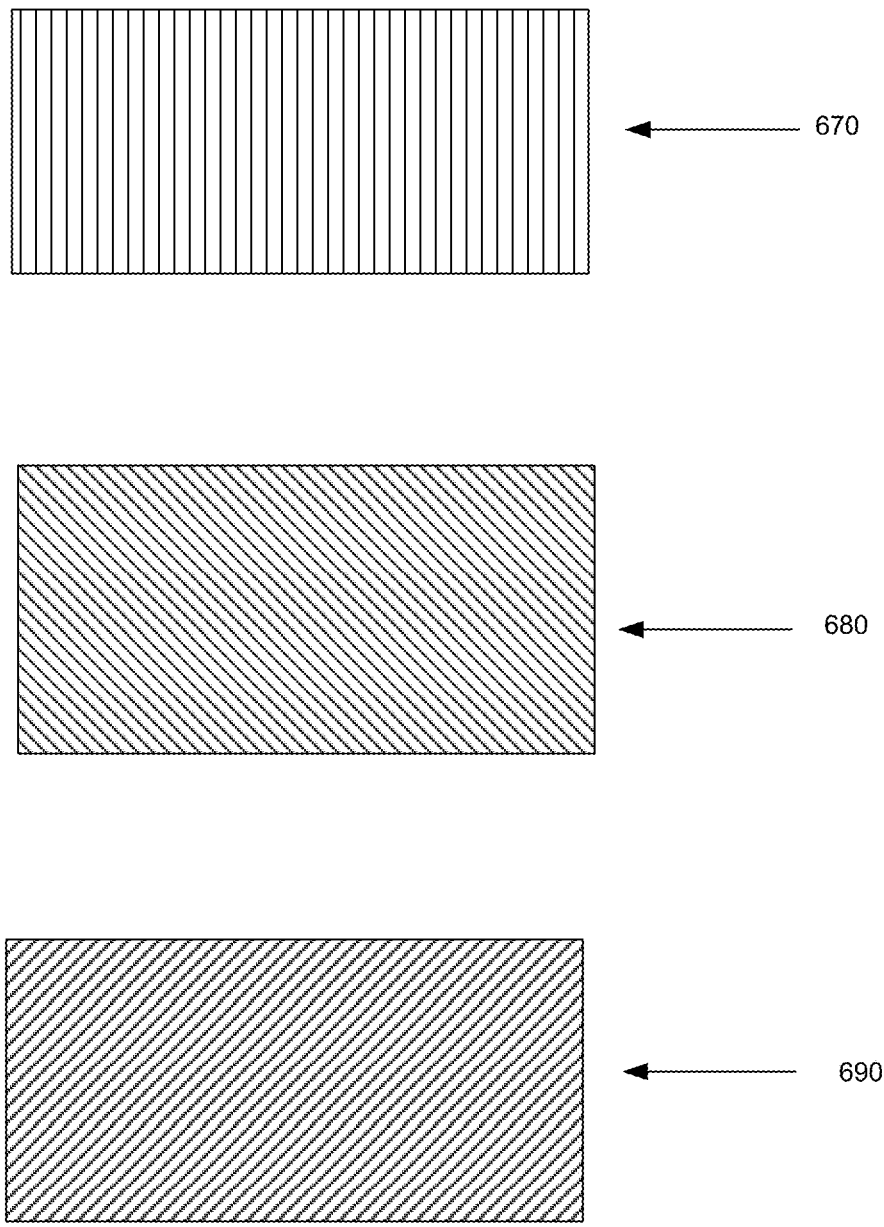
FIG. 16 illustrates various scanning orientations of an object by the handheld imaging apparatus of in FIGS. 14-15.

In the embodiments illustrated in FIGS. 5-13 and those depicted in FIGS. 14-16, the imaging systems are configured so that they are smaller, lighter, and handheld. In these embodiments, the handheld systems can still be used to create an image of a desired object using scattered radiation, including backscattered x-ray radiation. In the embodiments shown in FIGS. 5-13, the handheld imaging systems are configured with a cone beam of radiation that strikes the desired object. The backscattered radiation is then detected by multiple detector elements that are oriented differently and that are collimated. Multiple 2-D images can be collected simultaneously from the multiple detector elements and then used to create the 3D image.

Figure 5:
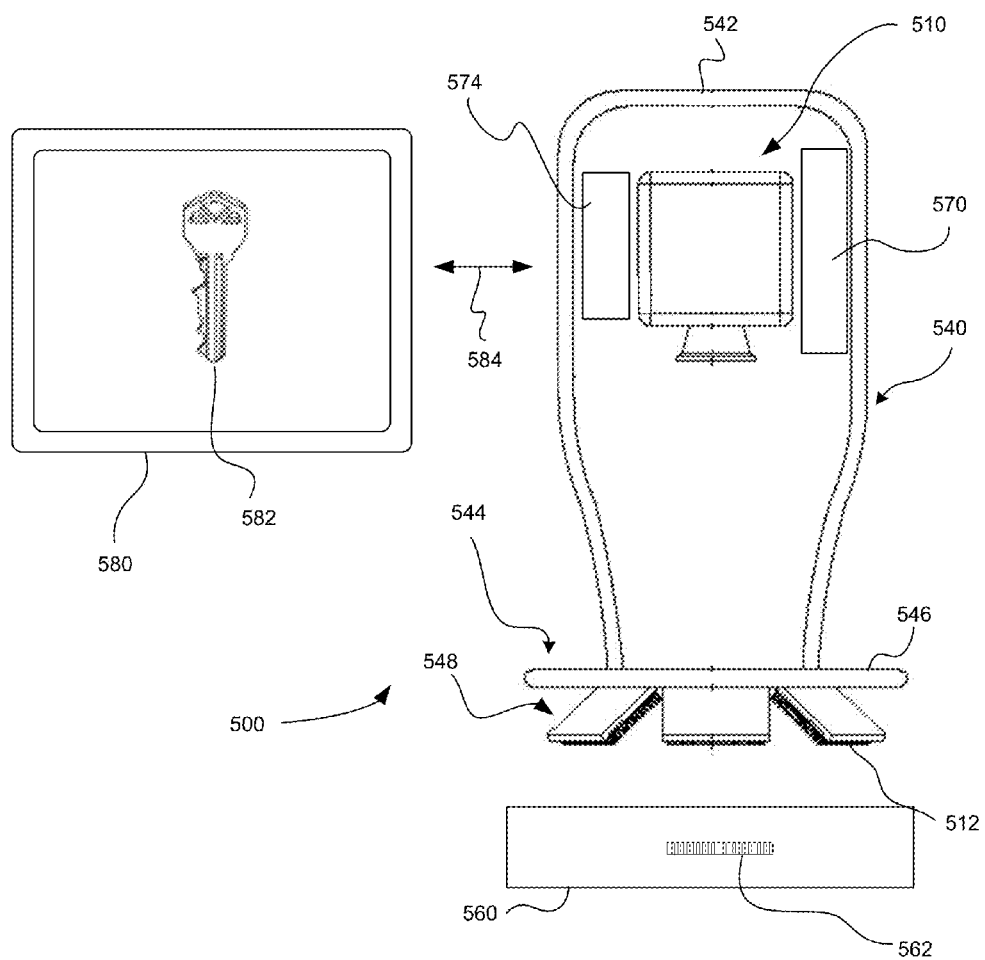
FIGS. 5 and 6 illustrate side views of some embodiments of a handheld imaging apparatus with a first configuration of detector elements.

Some configurations of these handheld imaging systems are configured in FIGS. 5-8. As shown in FIG. 5, the system 500 may include a hand-held x-ray device 540 and a display 580 to show an image 582 of the desired object 562 (often embedded in a matrix 560) that has been created using the hand-held device 540. The display 580 may communicate with the hand-held x-ray device 540 through a communication connection 584. The hand-held x-ray device connection 584 may be wired or wireless, and may be remote or local. Examples of some wireless transmission mechanisms include 802.11 protocols, wireless application protocols (WAP), Bluetooth technology, or combinations thereof.

Any display mechanism can be used as display 580. Examples of displays that can be used in the system 500 include films, imaging plates, and digital image displays such as cathode ray tubes (CRT), or liquid crystal display (LCD) screens. In some configurations, the display 580 can be integrated into the housing 542 of the x-ray device 540. Such integration, however, will limit the size of the display since too large a display can detract from the portability of the handheld device 540. In these integrated configurations, any small display with sufficient resolution can be used, including liquid crystal display (LCD) screens. In other configurations, the display can be located external to the x-ray device 540. In these configurations, a separate imaging plate (such as a CMOS or TFT plate) for larger features (such as medical or veterinary imaging) can be used. The separate imaging plate can be connected to the remainder of the x-ray device so that it receives the image to display. In some configurations, the display 580 can contain multiple displays with each display matched with a detector element (as described below).

Figure 6:
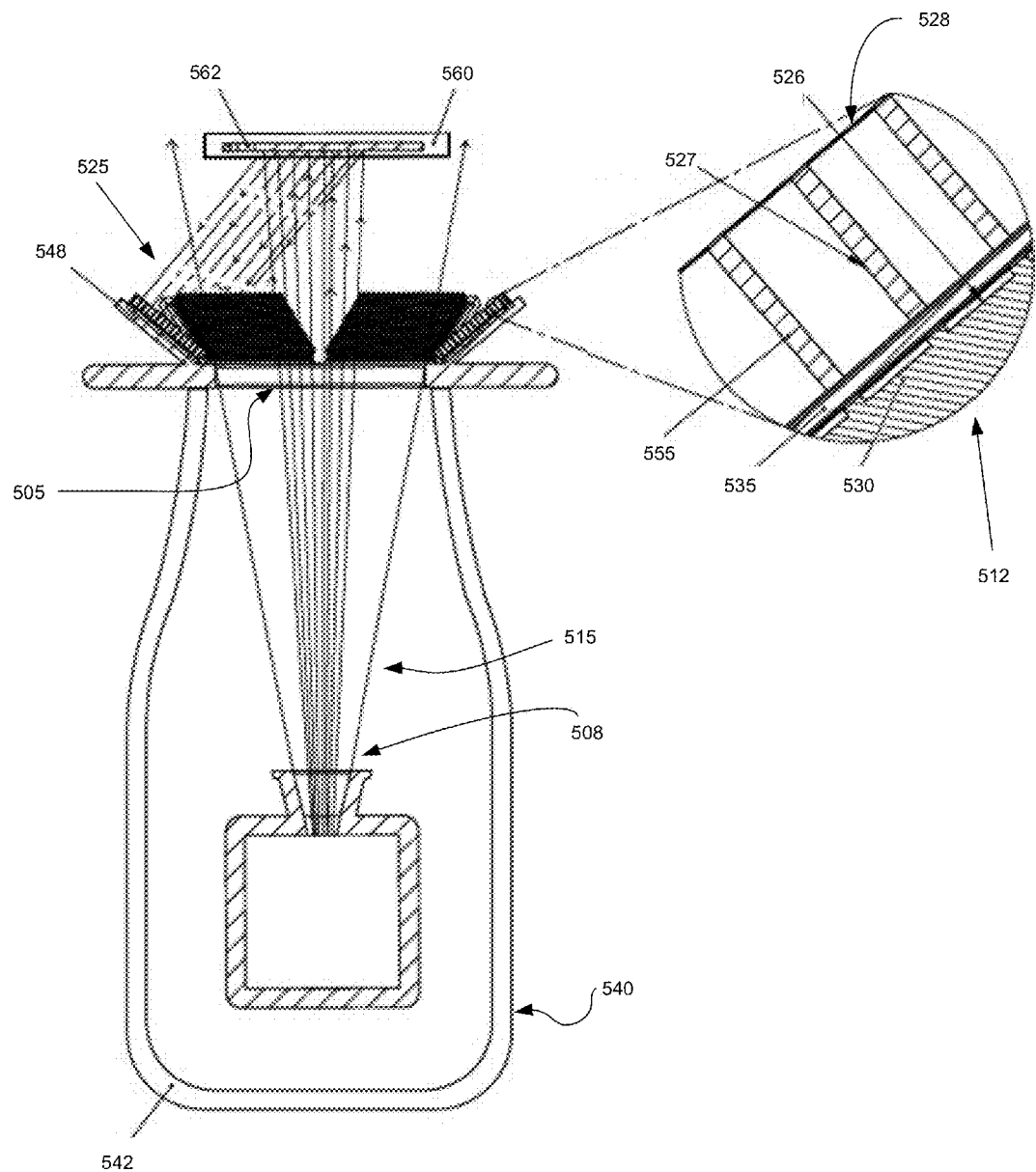

As shown in FIGS. 5-6, the x-ray device 540 contains a housing or chassis 542 enclosing all the internal components of the x-ray device 540. The housing 542 contains a window (or opening) 505 through which x-rays 515 are emitted and strike the desired object 562 embedded in the matrix 560. The window 505 can be configured for the desired object 562 so that the desired amount of x-rays 515 is emitted to strike the object 562. Thus, the window 505 can be configured to be smaller than, larger than, or about the same size as the desired object 562.

In the embodiments shown in FIG. 5, the x-ray device 540 may contain a base 544 with a partial shield 546. The partial shield 546 is located behind the detectors so that the detectors are not blocked while also partially protecting the user of the x-ray devices from backscattered radiation.

As best shown in FIG. 6, the device 540 contains an x-ray tube 510 which contains an x-ray source (not shown) for producing the emitted x-rays 515. The x-ray tube 510 contains an aperture 508 through which the x-rays are emitted from the x-ray source and into the x-ray device 540. In some configurations, the x-rays are emitted as a fan beam and so the aperture is configured accordingly. In other configurations, the x-rays are emitted as a cone beam, as shown in FIG. 6, and the aperture 508 is configured accordingly. Where a fan beam is used, the device 520 would have to scan the beam across the desired object so that the full sample area is illuminated and the user would have to collect the 2D images at each position of the fan beam and a large number of such 2D images would have to be collected. By using a cone beam, the user only need to collect one 2D image in each detector.

The x-ray device 540 also contains a power system 570 to provide power for the x-ray device 540. The power system 570 can contain both an internal power supply that is connected to an internal power source. Details of such a system are described in U.S. Pat. Nos. 7,496,178 and 7,224,769, the entire disclosures of which are incorporated herein by reference. In other configurations, the power source can be located external to the device.

The x-ray device 540 also contains any other components for efficient operation, such as a controller and other electronics (collectively depicted as electronics 574). Further details of such components are described in U.S. Pat. Nos. 7,496,178 and 7,224,769, the entire disclosures of which are incorporated herein by reference.

The x-ray device 540 also contains a detector for detecting or sensing the scattered radiation (i.e., x-rays) 525. Any detector that is sensitive to x-ray radiation (or the other types of radiation described herein) can be used in the handheld x-ray device 540. Examples of such detectors include x-rays receptors, x-ray film, CCD sensors, CMOS sensors, TFT sensors, imaging plates, image intensifiers, or combinations thereof.

Figure 7:
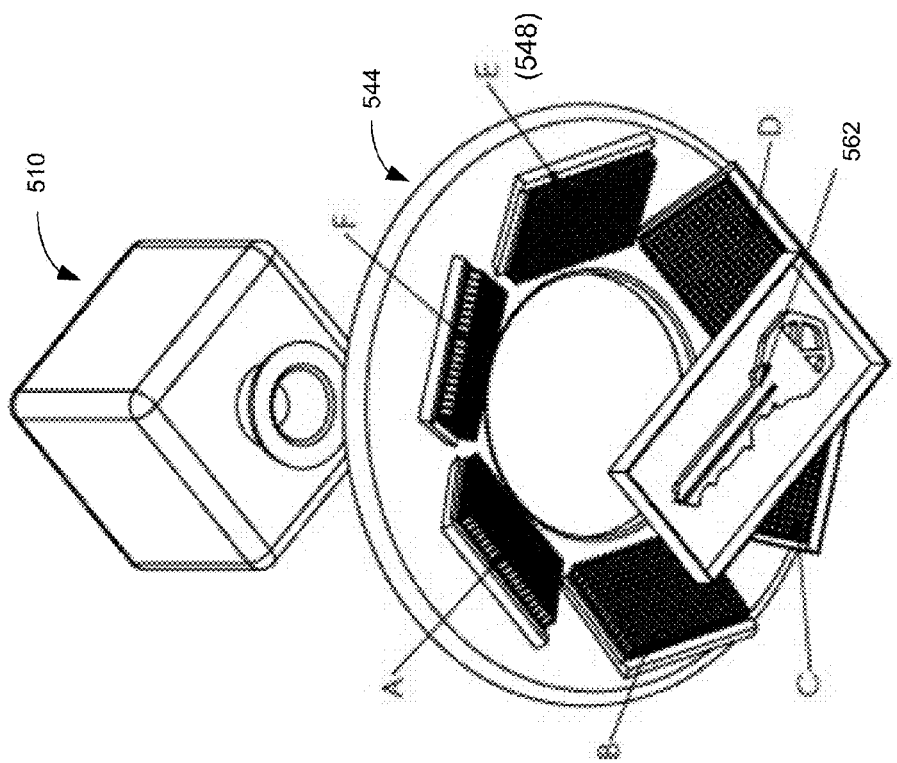
FIG. 7 illustrates a bottom view of some embodiments of a handheld imaging apparatus with a first configuration of detector elements.

In some configurations, the detector used in the x-ray device 540 comprises the detector elements 548 depicted in FIGS. 5, 6, and 7. In these configurations, the detector is separated into multiple detector elements 548 that are spaced around the object 562. The detector can be separated into any number of detector elements, with as few as 2 or as many as thousands or millions of pixels. In the illustrated embodiments, the detector has been separated into 6 detector elements 548 that are evenly spaced around the circumference of the object (i.e., every 60 degrees). In other embodiments, though, the detector elements 548 need not so be evenly spaced.

The individual detector elements 548 can all have substantially the same size or can have different sizes. In the illustrated embodiments, all of the detector elements 548 have substantially the same size. The size of the detector elements 548 can be based on the expected size of the desired object 562 being imaged.

The individual detector elements 548 can all have substantially the same shape or can have a different shape. In the illustrated embodiments, all of the detector elements have substantially the same rectangular shape. The shape of the detector elements used is based on the expected shape of the desired object 562 being imaged. In some embodiments, the detector elements can be any shape, include rectangular, square, annular, polygonal, circular, oblong, or any combination thereof.

In the embodiments shown in FIG. 6, the detector elements 548 can comprise an active detector pixel (i.e., a photodiode) 530 that has been placed on the bottom of a scintillator 535. In these embodiments, the active detector pixels 530 are sensitive to—and therefore detect—light. The scintillator 535 can be used to convert the backscattered x-rays 525 to light which then impinges on the active detector pixels 530. The active detector pixels 530 then display the light image they receive on the display 580 (or a portion thereof). Such embodiments can be useful because they can be cheaper to use than other x-ray detectors.

The x-ray device 540 also contains a collimator that separates each detector element into multiple detector segments that each detect radiation along a single path or line of sight. In the embodiments depicted in FIGS. 6-7, each detector element 548 is attached to one end of a collimator structure (or collimator) 512 that contains a series of grid elements 555. The collimator 512 can include any of a variety of cross sectional areas, including a cylindrical, elliptical (non-circular), or rectangular and can have any number of features with various geometries including fins, slats, screens, and/or plates that may be curvilinear or flat.

The backscattered radiation 525 from the object 562 reaches the detector elements 548 through the apertures 528 in the collimator 512. If the backscatter direction of the x-ray is substantially parallel to the direction of the collimator 512 or has a narrow enough angle to travel through the aperture 528 (as shown in FIG. 6 by beam 526), it will strike the scintillator 535 without being absorbed by the collimator grid elements 555. Non-substantially parallel x-ray beams (as shown by beam 527) will be absorbed by the collimator grid elements 555.

Accordingly, the collimator 512 can be configured with any size and shape that operates with the detector element 548 to absorb any off-axis backscattered x-rays while allowing substantially parallel oriented x-rays to strike the detector elements 548. The collimator 512 can also have any desired length or width for the grid elements 555. As well, the collimator 512 can be modified to allow for a wider aperture to allow in more backscattered radiation or a narrower aperture to decrease the backscattered radiation from the object.

In some configurations, the collimator 512 can be oriented substantially perpendicular to the surface of the detector elements 548. These configurations are illustrated in FIG. 6 where each collimator grid element 555 is oriented substantially perpendicular to the detector elements 548.

Figure 8:
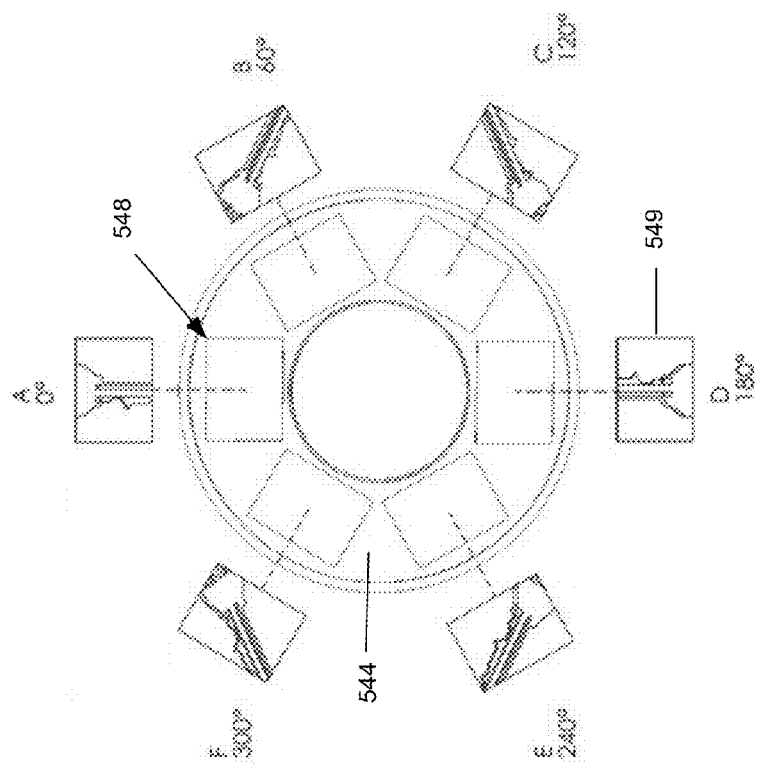
FIG. 8 illustrates a bottom view of some embodiments of a handheld imaging apparatus with a first configuration of detector elements along with the images shown by the detector elements.

In these configurations, the parallel-plate collimator restricts the field of view of each detector segment to a single line of sight to the desired object 562. Thus, each detector element 548 (i.e., A through F) has a different view of the key, as shown in FIG. 8. For example, where the object to be imaged is a key, FIG. 8 illustrates that each different detector element captures and can display a different image 549 of the key.

Figure 10:
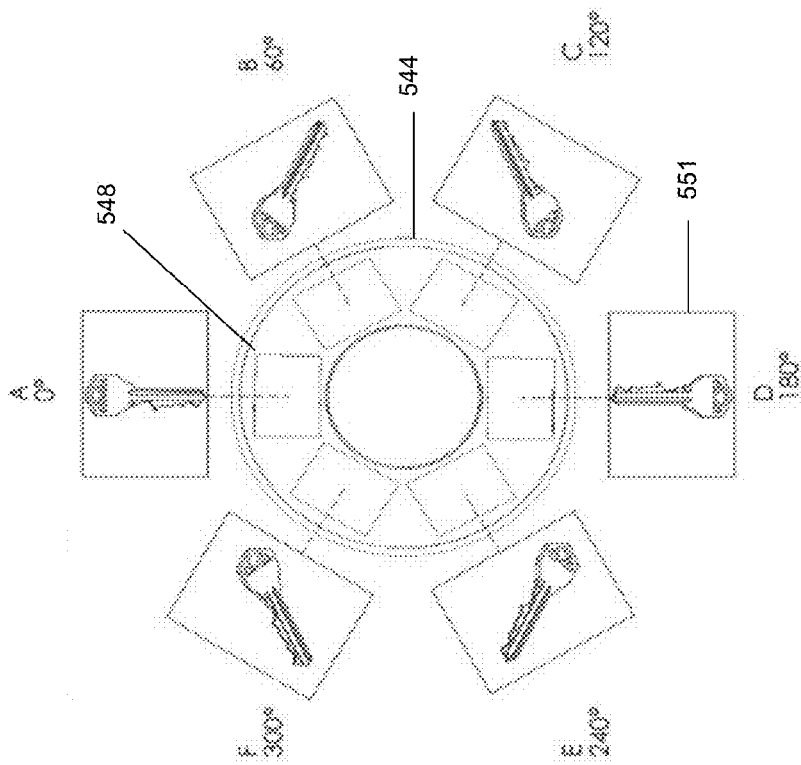
FIG. 10 illustrates a bottom view of some embodiments of a handheld imaging apparatus with a second configuration of detector elements along with the images shown by the detector elements.
Figure 9:
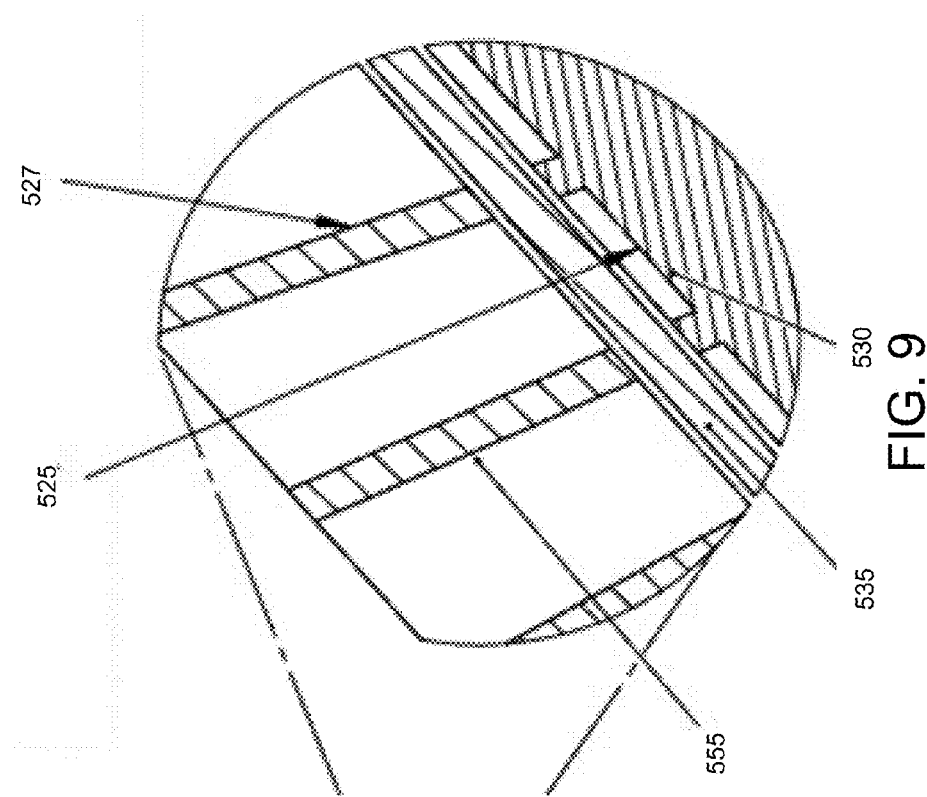
FIG. 9 illustrate side views of some embodiments of a handheld imaging apparatus with a second configuration of detector elements.

In other configurations, though, the collimator features can be given a non-parallel orientation. One example of a non-parallel orientation of the collimator is illustrated in FIG. 9, where the collimator features are configured so that they have a focusing orientation so that they focus the backscattered radiation on the detector elements. With a focusing orientation, the open end of the collimator 512 (nearer the object 562) has a width larger than the width at the opposite end of the collimator (where it connects with the scintillator 535). This focusing orientation can be useful when each detector element needs a more complete image 551 of the desired object, as shown in FIG. 10. Such images can be compared to FIG. 8 where the image of the key 549 on the detector element is cut off because each detector element 548 is smaller than the object to be imaged (key). This smaller image results from the parallel plate collimator because it only allows the detector to "see" a field of view that is the size of the detector element.

To obtain a more complete image of the key, other configurations of the handheld device 540 configures the detector elements 548 to be larger. But increasing the size of the detector element is not always possible. So instead, the focusing orientation of the collimator features can be used to provide a wider field-of-view for each detector segment. But with the focusing orientation, the image resolution can be worse than the parallel plate orientation because the wider aperture opening on the sample end of the collimator allows a wider incident angle for the backscattered photons from the sample surface. Whether to use a parallel plate orientation or a focusing orientation will depend on the size of the object to be imaged, the size of each detector element, the need to increase the flux, or the need to maintain the best possible spatial resolution.

In other configurations, though, the collimator can have a reverse-focusing orientation. With a reverse-focusing orientation, the open end of the collimator has a width smaller than the width at the opposite end of the collimator. This reverse focusing orientation can be useful when better spatial resolution is required.

Figure 11:
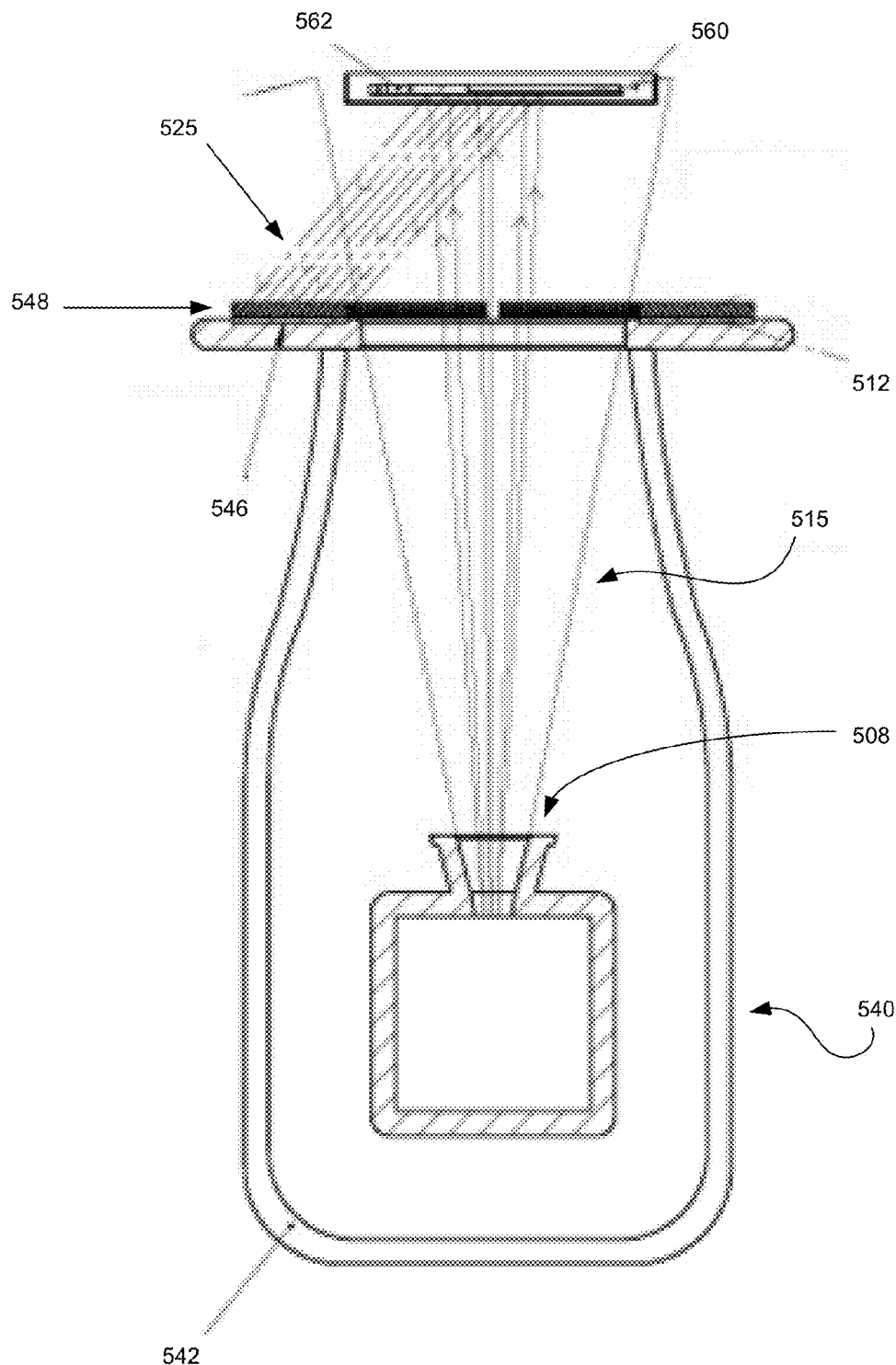
FIG. 11 illustrates a side view of some embodiments of a handheld imaging apparatus with a third configuration of detector elements.
Figure 13:
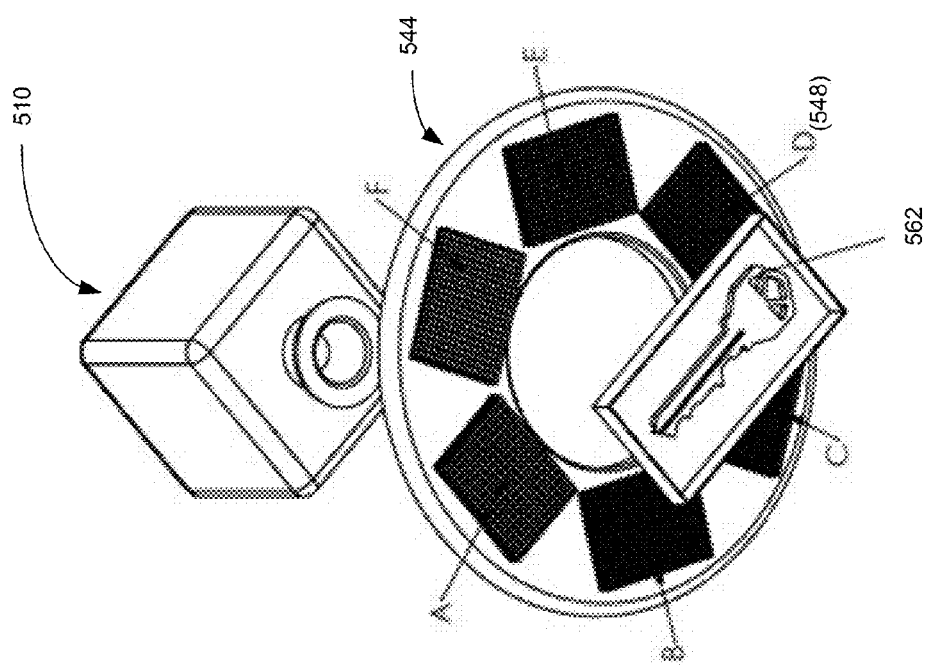
FIGS. 12 and 13 illustrate bottom views of some embodiments of a handheld imaging apparatus with a third configuration of detector elements.

In other embodiments, the detector elements 548 can be disposed on a plane that is substantially parallel to the plane of the object 562 being analyzed. These embodiments are depicted in FIG. 11 where the detector elements 548 can be disposed on a plane substantially parallel to the key 562. This configuration may allow the detector elements 548 to be positioned closer to the key 562, which can improve the signal to noise ratio and allow for a shorter collection time. The image resolution can also be improved in these embodiments since the divergence of each backscattered x-ray beam 525 is a function of the distance from the collimator 512 to the key. At long distances, the spatial resolution can be degraded due to overlapping field of view for each detector pixel 530. This effect can be minimized by locating the detector elements 548 as close as possible to the object 562 to be imaged.

The distance between the device and the desired object is, in part, a function of the image distance from the end of the collimator as a ratio of the collimator thickness. Closer distances give a better surface resolution while locating the device farther away allows a steeper angle for the detector, which yields better depth resolution.

Figure 12:
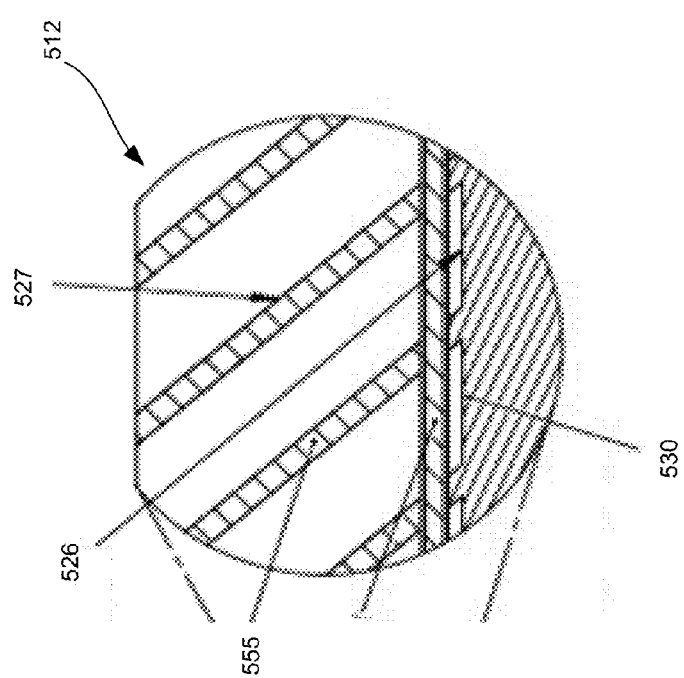

In these embodiments, the collimator grid elements 555 can be angled to allow each detector element 548 to view substantially the same field of view of the object, as shown in FIG. 12. By changing the orientation of the detector elements 548, the orientation of the collimator 512 has to be changed correspondingly so that only substantially parallel x-rays 526 are transmitted through—and off-axis x-rays 527 are absorbed by—the collimator 512.

In the embodiments shown in FIG. 12, the collimator features are still oriented substantially parallel to each other. This configuration provides a substantially 1:1 view of the object. In other embodiments, though, a reverse-focusing collimator can be used to achieve geometrical magnification on the detector (with degraded spatial resolution). In still other embodiments, focusing collimators can be used to achieve optimum spatial resolution over a smaller field of view.

The specific angle of the collimator 512 in these embodiments is selected based on the distance between the x-ray device 540 and the object 562 which, in turn, can determine the angle (relative to the detector element 548) of the backscattered radiation. The smaller this distance, the smaller the angle of the backscattered radiation and the smaller the angle of the collimator (relative to the plane of the detector element). The larger this distance, the larger the angle of the backscattered radiation and the larger the angle of the collimator.

The detector elements 548 can have different configurations. For examples, the detector elements can have different shapes, different sizes, and different angles. This allows them to capture different images of the desired object, which can still be used to create a 3D image provided the reconstruction algorithm is modified accordingly. In some embodiments, the detector elements can be configured so that they individually or collectively lower and raise, i.e., move along any angle and from a flat position to an angled position. The collimator can likewise be configured so that it can change angles as needed.

The different images collected by the detector elements can then be used to create a 3D image. The multiple 2D views of the same location on the sample that are collected can be used by a 3-D reconstruction algorithm to achieve 3-D images of the object that is imaged similar to the methods described herein.

Virtually any object that is small enough can be imaged by the handheld x-ray devices described herein. Of course, larger objects can be imaged, by the handheld x-ray device would become larger and heavier and at some point, would cease to be handheld even though it is still portable.

In some embodiments, the object 562 to be imaged (such as the illustrated key) can be embedded in a matrix 560. The matrix 560 can be made of plastic or other material having a sufficiently different density from the key so that the backscatter signal is significantly different from the object 562 than from the matrix material. In other embodiments, though, the object need not be embedded in such a matrix. Each detector element 548 can provide a different view of the object 562, as discussed above. By utilizing the multiple different images, along with a 3-D reconstruction algorithm, a 3-D image 582 of the object can be obtained and displayed on the display 580.

The 3-D backscatter x-ray imaging with a handheld device 540 provides an advantage relative to some current devices and methods in that they can be easily transported and used by a single operator, can be held in place while the image is being collected, and the 3-D image reconstruction allows the operator to obtain depth information that is not available in a 2-D image. Similarly, because the device is hand-held and the 3-D image may be provided in real time, the device may be adjusted and manipulated to provide different view of the object being viewed. This flexibility in use may provide for additional confidence in assessing the nature of the object. For example if a user is inspecting an airframe for stress, the ability to explore any anomalies from different viewpoints may provide for increased safety and decreased downtime for the aircraft.

These handheld devices 540 are significantly lighter than the devices described in FIG. 1-4. This decreased weight is due to that fact that the handheld devices 540 contain no motor for rotation, because the handheld devices 540 contain much smaller detectors, and because they can contain a low-power battery-powered x-ray module.

These handheld x-ray devices 540, however, suffer from the drawback that the use of a collimator can result in high dosages. Collimating the x-rays in these devices can cause difficulties because only a small amount of radiation can impinge on the detector elements. With less radiation striking the detector, the x-ray dosage has to be increased and the size of the x-ray tube has to be increased in order to obtain the desired image resolution. But increased x-ray dosages can lead to safety problems.

To overcome these drawbacks, the handheld x-ray devices can be modified with other configurations that do not use collimators. These embodiments are illustrated in FIGS. 14-16. In these embodiments, the handheld x-ray device 640 contains a base 660, housing 642 enclosing the x-ray tube 610, power system 670, and electronics 674 similar to the embodiments described in FIGS. 5-13. The handheld x-ray device 640, however, uses a moving pencil beam 605 of x-ray radiation instead of a cone beam. This moving pencil beam 605 can be created by limiting the aperture of the x-ray tube 610 to a very small size and/or by limiting the window 620 of the x-ray device 640 to the desired width of the pencil beam. As well, if needed, a collimator (not shown) can be placed between the x-ray device 640 and the desired object to limit the size and orientation of the x-ray beam as shown in FIG. 14. As shown in FIGS. 14-15, the moving pencil beam 605 is emitted from different locations of the aperture of the x-ray tube 610 and so can emerge from the handheld device 640 with multiple orientations that can be used to raster-scan the desired object 562.

The x-ray devices 640 in these embodiments also contain multiple detectors. In the configurations illustrated in FIG. 14, the x-ray device 640 contains multiple, un-collimated, discrete detectors 648 that are attached to a support 646 of the device 640. The detectors 648 can have any shape or size, including those described herein. The detectors 648 can be also located off-axis with respect to the x-ray source within the x-ray tube 610. In other words, the detectors 648 can be located at an angle relative to the x-ray beam 605. In some configurations, the detectors 648 in these configurations can be much larger than the multiple detector elements illustrated in FIGS. 5-13.

As the pencil beam is raster scanned across the surface of the sample, the backscatter x-ray intensity is measured on each detector 648 as a function of the beam position. Since the incident x-ray beam is illuminating a single volume within the sample, differences in intensity from detector to detector are indicative of the absorbing material in the beam path from the scattering location to the detector. By collecting the scattered intensity from multiple detector angles, 3D reconstruction techniques can be used to determine the density of the absorbing material in the beam paths. That information can be used to reconstruct a full 3D volume image of the total irradiated sample volume.

In the embodiments shown in FIG. 14, the multiple detectors 648 comprise multiple concentric circles located outward from the window 620. Each of the detectors are discrete from each other so that they detect the samples at different angles. While there are two detectors illustrated in FIG. 14, the device 640 could contain any numbers of detectors (i.e., 3, 4, 5, 6, etc.).

In other embodiments, the handheld x-ray device 640 contains the multiple, un-collimated, discrete detectors 648 as shown in FIG. 15. Any number of large detectors can be used, including as few as 2 (as illustrated) and as many as desired in the final handheld device given the size and weight restrictions of the handheld operation. In some configurations, an array of 6 detectors can be used similar to those shown in FIGS. 5-13 but without the collimators. These detectors 648 can be oriented so that the backscattered radiation 625 from the object 562 will impinge on them.

In these embodiments, the pencil x-ray beam 605 will be raster-scanned in 2 dimensions across the desired object 562. This raster-scanning action will be performed in a first orientation 670 as shown in FIG. 16 to collect a first series of 2D backscatter images. The number of images will be the same as the number of detectors used. So if there are 6 detectors, 6 2D backscatter images will be collected. These six 2D images can be used to can be used to reconstruct a full 3D volume image of the total irradiated sample volume.

Even though with multiple detectors there is no need to move the device to a $2^{nd}$ orientation, in some embodiments this action can be performed. In these embodiments, the handheld device 640 will then be rotated and the raster-scanning action will be performed in a second orientation 680 as shown in FIG. 16 to collect a second series of 2D backscatter images. The handheld device 640 can then be rotated and the raster-scanning action will be performed in a third orientation 690 as shown in FIG. 16 to collect a third series of 2D backscatter image. Additional rotations and scanning processes can be performed, as needed to increase the image resolution.

Since the detector and source are positioned off-axis, multiple 2-D images can be obtained. Using 3-D computed tomography algorithms substantially similar to those described above, a 3-D image can be obtained by the reconstruction of the 3-D volume from these 2-D projections. This multiple image collection can occur at various angles, resulting in a 3-D volume reconstruction as described in detail above.

In some embodiments, a method of imaging an object comprises: providing a handheld apparatus for imaging an object containing a radiation source for irradiating an object with a raster scan pencil beam of radiation and multiple detectors configured to detect scattered radiation from the object, wherein the detectors and the radiation source are oriented off-axis relative to each other; raster scanning the object with the handheld apparatus to obtain a series of two dimensional images of the object; and creating a three dimensional image of the object using the series of two dimensional images. In this method of claim, the multiple detectors are configured to collected multiple 2D images at various angles.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A handheld apparatus for imaging an object, comprising:
 a radiation source for irradiating an object with a cone beam; and
 multiple detector elements for detecting scattered radiation from the object, wherein each detector element has a different view of the object and collects an image of the object that is different than the other detector elements so that multiple two-dimensional images of the entire object are taken substantially simultaneously.

2. The apparatus of claim 1, wherein the handheld apparatus comprises a collimator for separating each detector element into detector segments.

3. The apparatus of claim 2, wherein the collimator comprises a grid that restricts the backscattered radiation impinging on each detector segment.

4. The apparatus of claim 1, wherein the multiple images are collected substantially at the same time.

5. The apparatus of claim 1, wherein each detector element has an adjustable orientation angle with respect to the plane of object.

6. The apparatus of claim 5, wherein the orientation angle is about 0 degrees so that some of the multiple detector elements are disposed on a plane substantially parallel to the object plane.

7. The apparatus of claim 1, further comprising a housing enclosing the radiation source and enclosing an internal power source.

8. The apparatus of claim 2, wherein the collimator comprises a reverse-focusing collimator.

9. The apparatus of claim 2, wherein the collimator comprises a focusing collimator.

10. The apparatus of claim 2, wherein the collimator comprises a parallel plate collimator.

11. A method of imaging an object, comprising:
 providing a handheld apparatus for imaging an object containing a radiation source for irradiating an object with a cone beam, and multiple detector elements for detecting scattered radiation from the object, wherein each detector element has a different view of the object and collects an image of the object that is different than the other detector elements so that multiple two-dimensional images of the entire object are taken substantially simultaneously;

irradiating the object with the handheld apparatus to obtain multiple two dimensional images of the object; and creating a three dimensional image of the object using the multiple two dimensional images.

12. The method of claim 11, wherein the handheld apparatus comprises a collimator for separating each detector element into detector segments.

13. The method of claim 12, wherein the collimator comprises a parallel plate collimator, a reverse-focusing collimator, or a focusing collimator.

14. The method of claim 11, wherein each detector element has an adjustable orientation angle with respect to the plane of object.

15. The method of claim 14, wherein the orientation angle is about 0 degrees so that some of the multiple detector elements are disposed on a plane substantially parallel to the object plane.

16. The apparatus of claim 14, wherein the handheld apparatus further includes a housing enclosing the radiation source and enclosing an internal power source.

* * * * *